United States Patent
Kawaguchi et al.

(10) Patent No.: US 10,488,534 B2
(45) Date of Patent: Nov. 26, 2019

(54) PORTABLE RADIATION IMAGE CAPTURING APPARATUS

(71) Applicant: Konica Minolta, Inc., Tokyo (JP)

(72) Inventors: Manabu Kawaguchi, Hachioji (JP); Kohei Miyoshi, Hachioji (JP); Makoto Sumi, Tokorozawa (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 16/078,885

(22) PCT Filed: Oct. 27, 2016

(86) PCT No.: PCT/JP2016/081817
§ 371 (c)(1),
(2) Date: Aug. 22, 2018

(87) PCT Pub. No.: WO2017/145443
PCT Pub. Date: Aug. 31, 2017

(65) Prior Publication Data
US 2019/0018151 A1    Jan. 17, 2019

(30) Foreign Application Priority Data
Feb. 22, 2016  (JP) ................... 2016-031005

(51) Int. Cl.
*G01T 1/24*    (2006.01)
*A61B 6/00*    (2006.01)
(Continued)

(52) U.S. Cl.
CPC ............ *G01T 1/244* (2013.01); *A61B 6/00* (2013.01); *A61B 6/4283* (2013.01);
(Continued)

(58) Field of Classification Search
CPC .................. G01T 1/244; G01T 7/00
(Continued)

(56) References Cited

U.S. PATENT DOCUMENTS 5,811,790 A * 9/1998 Endo ............ H01L 27/1446
250/208.1
2012/0018644 A1* 1/2012 Caruba ............ G01R 33/481
250/362
(Continued)

FOREIGN PATENT DOCUMENTS

JP    S64-22093 U    2/1989
JP    H09-288184 A    11/1997
(Continued)

OTHER PUBLICATIONS

English Abstract JP 2007-194519 (Year: 2007).*
(Continued)

*Primary Examiner* — David P Porta
*Assistant Examiner* — Abra S Fein
(74) *Attorney, Agent, or Firm* — Lucas & Mercanti, LLP

(57) ABSTRACT

A portable radiography device includes a housing with a front plate, a back plate, and a sensor panel accommodated therein. Electronic components disposed on the back plate side of the sensor panel are used to read a charge generated by the radiation detection element as a signal value and generate heat when reading the signal value. A heat conduction member is pressed by the back plate and the electronic components resulting in close contact of the heat conduction member with the electronic components and the back plate.

13 Claims, 5 Drawing Sheets

(51) Int. Cl.
    *G01T 7/00*     (2006.01)
    *G01T 1/20*     (2006.01)
    *G03B 17/55*     (2006.01)
    *G03B 42/04*     (2006.01)

(52) U.S. Cl.
    CPC .............. *G01T 1/2018* (2013.01); *G01T 7/00* (2013.01); *G03B 17/55* (2013.01); *G03B 42/04* (2013.01)

(58) Field of Classification Search
    USPC .................................................. 250/370.15
    See application file for complete search history.

(56) References Cited

U.S. PATENT DOCUMENTS

| | | | |
|---|---|---|---|
| 2012/0027364 A1* | 2/2012 | Tamura | G02B 6/4201 385/92 |
| 2013/0038738 A1* | 2/2013 | Ando | A61B 6/4266 348/162 |

FOREIGN PATENT DOCUMENTS

| | | | |
|---|---|---|---|
| JP | H10-65385 A | | 3/1998 |
| JP | H11-163566 A | | 6/1999 |
| JP | 2002131437 A | | 5/2002 |
| JP | 2003194951 A | | 7/2003 |
| JP | 2007-194519 | * | 8/2007 |
| JP | 2011043390 A | | 3/2011 |

OTHER PUBLICATIONS

English Translation JP 2003-194951 (Year: 2003).*
English Translation JP 2011-43390 (Year: 2011).*
Written Opinion of the International Searching Authority dated Dec. 27, 2016 from corresponding International Application No. PCT/JP2016/081817 and English translation.
International Search Report dated Dec. 27, 2016 for PCT/JP2016/081817 and English translation.

* cited by examiner

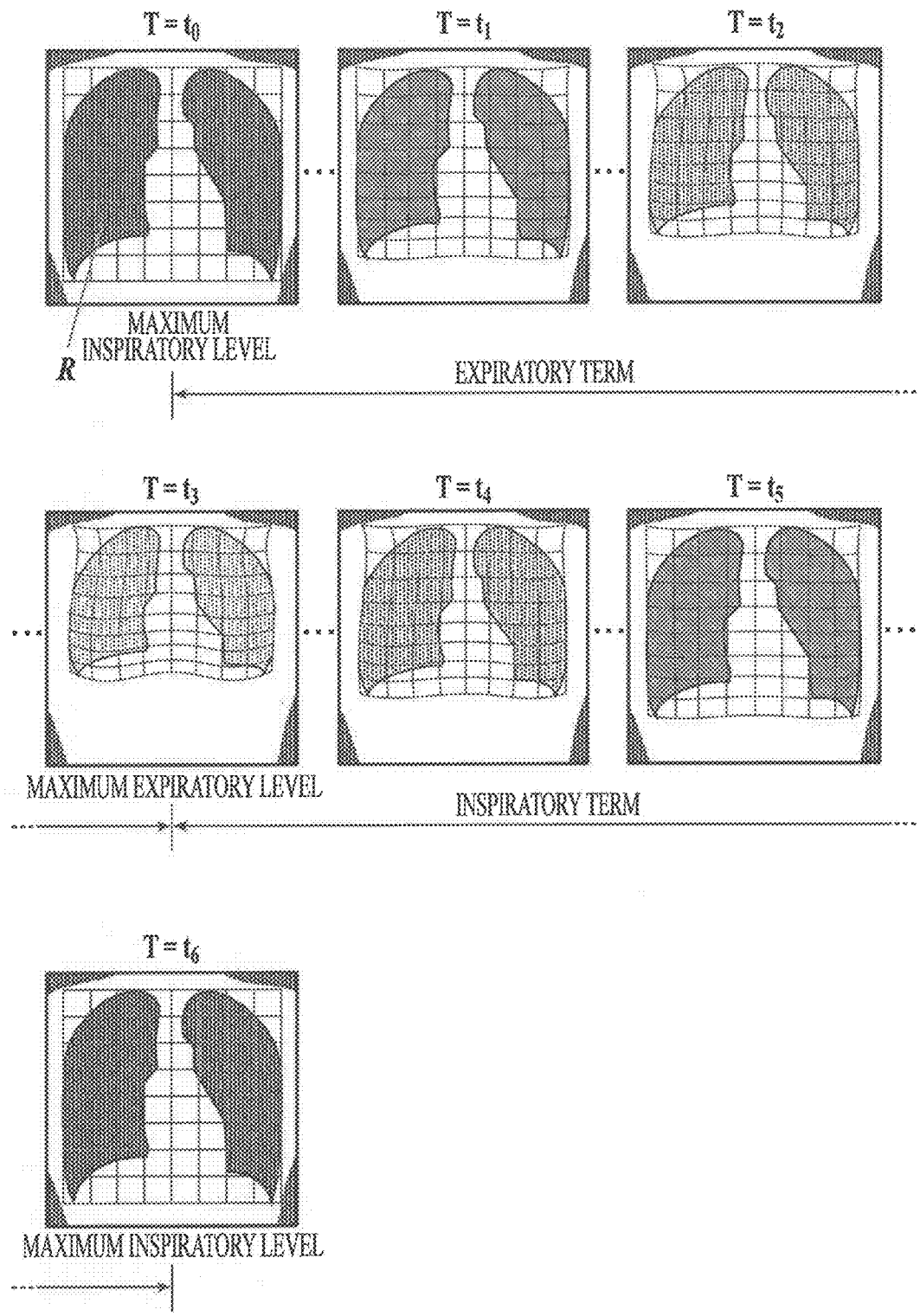

PORTABLE RADIATION IMAGE CAPTURING APPARATUS

CROSS REFERENCE TO RELATED APPLICATION

This application is a 371 of PCT/JP2016/081817 filed on Oct. 27, 2016 which, in turn, claimed the priority of Japanese Patent Application No. 2016-031005 filed on Feb. 22, 2016, both applications are incorporated herein by reference.

TECHNOLOGICAL FIELD

The present invention relates to a portable radiation image capturing apparatus.

BACKGROUND ART

A radiation image capturing apparatus (flat panel detector, also called a semiconductor image sensor) is developed. In such radiation image capturing apparatus, a plurality of radiation detecting elements are arranged two-dimensionally (matrix shape), charge is generated in the plurality of radiation detecting elements according to the amount of radiation which passes to the subject and is irradiated on the element, and a readout IC reads the charge as a signal value. A portable radiation image capturing apparatus (also called a FPD cassette) is developed. In such portable radiation image capturing apparatus, a sensor panel in which a plurality of radiation detecting elements are arranged is stored in a case.

Then, when radiation is irradiated a plurality of times on the conventional film/screen and stimulable phosphor plate, the problem of double exposure and multiple exposure occurs. However, the radiation image capturing apparatus reads out the signal value each time capturing is performed, and the signal value can be stored in the memory of the apparatus or transferred outside. Therefore, by using the radiation image capturing apparatus, the radiation can be irradiated a plurality of times on the capturing site of the subject, and moving image capturing such as dynamic capturing can be performed.

For example, when radiation is irradiated a plurality of times on a chest portion of a subject as the capturing site and dynamic capturing is performed, for example, as shown in FIG. 7, radiation images (that is, each frame image composing the dynamic capturing) showing the time phases T ($T=t_0-t_6$) of a lung field R of the patient can be obtained. By analyzing the frame images, it is possible to obtain a maximum inspiratory level, a maximum expiratory level, an expiratory term, and an inspiratory term of the lung field R. Attempts are made to further analyze the dynamic image to be applied to diagnosis.

When the readout process of the signal value is performed in the radiation image capturing apparatus, electronic component such as the above-described readout IC and the power source circuit may generate heat. For example, when the readout IC generates heat, the signal value read out as described above with the readout IC may change due to the heat, and the radiation image may not be suitably captured. The captured radiation image may be blurred due to the heat of the readout IC and the power supply circuit and this may worsen the quality of the image.

Therefore, for example, Patent Document 1 discloses a radiation image capturing apparatus in which one end of a heat releasing member formed from a metallic material with a high thermal conductivity such as aluminum and copper is connected to an electronic component in the radiation image capturing apparatus, and the other end of the heat releasing member is attached to the inner side of a case. The heat from the electronic component is released to the case through the heat releasing member. With this, the temperature of the electronic component rising can be prevented.

PRIOR ART DOCUMENT

Patent Document

Patent Document 1: Japanese Patent Application Laid-Open Publication No. 2003-194951

SUMMARY

Problems to be Solved by the Invention

However, according to the configuration described in cited document 1, since the heat releasing member connecting the electronic component with the case is relatively long, the heat from the electronic component may be released to the inside of the case from the heat releasing member while transmitting through the heat releasing member before reaching the case. With this, the temperature of the space inside the case may rise, and the efficiency of releasing the heat of the electronic component to the outside of the case may not be high.

This problem may occur in simple capturing (that is, capturing in which radiation is irradiated to the radiation image capturing apparatus once, and one radiation image is obtained). However, in moving image capturing such as the above-described dynamic capturing, the readout process of the signal value is repeatedly performed. Therefore, compared to simple capturing, the electronic component such as the readout IC, etc. may generate more heat when the signal value is read out. Consequently, the problem becomes more noticeable.

Therefore, it is desired in a portable radiation image capturing apparatus which is able to perform moving image capturing that when the signal value is read out, the heat of the electronic components such as the readout IC and the power supply circuit is efficiently released to the outside of the case and the efficiency of releasing the heat of such electronic components to the outside of the case is enhanced.

The present invention is conceived in view of the above points, and the purpose of the present invention is to provide a portable radiation image capturing apparatus which is able to enhance the efficiency of releasing the heat of the electronic component to the outside of the case.

Means for Solving the Problem

To achieve at least one of the abovementioned objects, according to an aspect of the present invention, a portable radiation image capturing apparatus reflecting one aspect of the present invention is provided with a sensor panel in which a plurality of radiation detecting elements are arranged two-dimensionally and a case which is formed with a front plate on a side where radiation enters and a back plate on an opposite side, wherein the sensor panel is stored in the case, the portable radiation image capturing apparatus including: an electronic component which is provided on the back plate side of the sensor panel and which generates heat when charge generated in the radiation detecting element is read out as a signal value; and a heat conductive member which is provided between the electronic component and the back plate, wherein the heat conductive member is positioned pressed between the back plate and the electronic component in a state in which the heat conductive member is in close contact with the electronic component and the heat conductive member is in close contact with the back plate.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 7 is a diagram showing an example of frame images captured in dynamic capturing of a chest of a patient.

EMBODIMENT FOR CARRYING OUT THE INVENTION

Hereinafter, one or more embodiments of the present invention will be described with reference to the drawings. However, the scope of the invention is not limited to the disclosed embodiments.

An embodiment of a portable radiation image capturing apparatus according to the present invention is described with reference to the drawings.

Hereinbelow, the portable radiation image capturing apparatus may simply be referred to as a radiation image capturing apparatus. The example below describes an indirect type radiation image capturing apparatus which is provided with a scintillator and in which irradiated radiation is converted to electromagnetic waves with other wavelengths such as visible light to obtain an electric signal. Alternatively, a direct type radiation image capturing apparatus in which radiation is directly detected with a radiation detecting element without the scintillator can be applied to the present invention.

[Circuit Configuration of Radiation Image Capturing Apparatus]

Figure 1:
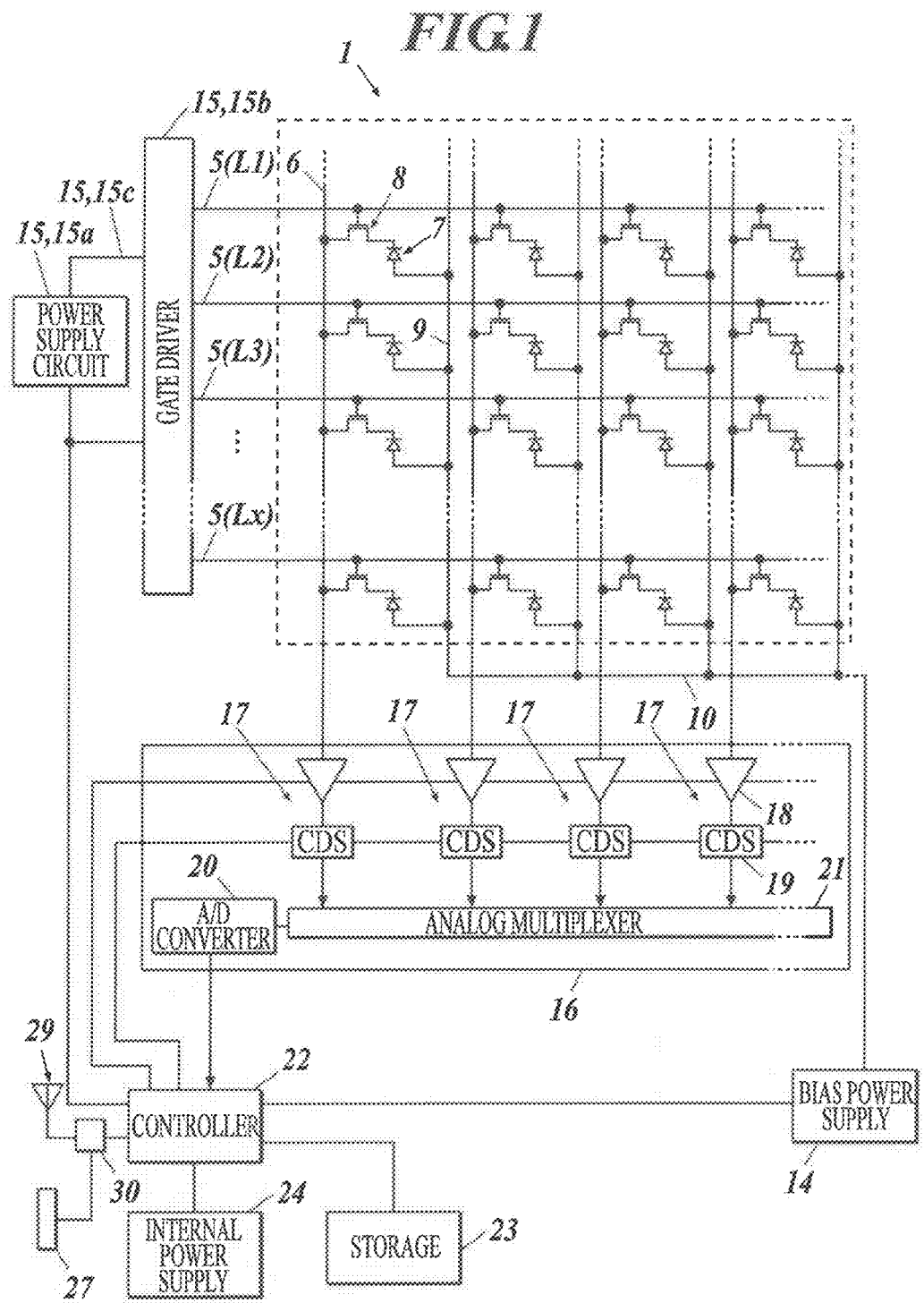
FIG. 1 is a block diagram showing an equivalent circuit of a portable radiation image capturing apparatus according to the present embodiment.

First, the circuit configuration of the radiation image capturing apparatus according to the present embodiment is described. FIG. 1 is a block diagram showing an equivalent circuit of the radiation image capturing apparatus according to the present embodiment. As shown in FIG. 1, the radiation image capturing apparatus 1 includes a plurality of radiation detecting elements 7 arranged two-dimensionally (matrix state) on a later-described sensor substrate 50 (see later-described FIG. 3, etc.).

The radiation detecting elements 7 are connected to bias lines 9 and reverse bias voltage from the bias power supply 14 is provided on the radiation detecting element 7 through the bias lines 9 and the connecting lines 10 connecting the bias lines 9. The radiation detecting elements 7 are connected to a TFT 8 (Thin Film Transistor) as a switch element and the TFT 8 is connected to a signal line 6.

In a scanning driver 15, on voltage and off voltage supplied from a power supply circuit 15a through a line 15c are switched with a gate driver 15b and applied to lines L1 to Lx of the scanning line 5. The TFTs 8 are in an off state when off voltage is applied through the scanning line 5, the conduction between the radiation detecting element 7 and the signal line 6 is cut, and the charge is accumulated in the radiation detecting element 7. The TFTs 8 are in an on state when the on voltage is applied through the scanning line 5, and the charge accumulated in the radiation detecting element 7 is discharged to the signal line 6.

Each of the signal line 6 is connected to each readout circuit 17 in the readout IC 16. In a readout process of a signal line D, when on voltage is applied to one line L in the scanning line 5 from the gate driver 15b, the TFT 8 is in an on state, the charge from the radiation detecting element 7 flows in the readout circuit 17 through the TFT 8 and the signal line 6, and an amplifying circuit 18 outputs a voltage value according to the amount of charge that flowed in.

A correlated double sampling circuit (described as "CDS" in FIG. 1) 19 reads out and outputs the voltage value output from the amplifying circuit 18 as a signal value D in an analog value. As described above, according to the present embodiment, the readout circuits 17 of the readout IC 16 reads the charge generated in the radiation detecting element 7 according to the amount of irradiated radiation as the signal value D.

The signal values D output from the amplifying circuit 18 are sequentially transmitted to a A/D converter 20 through an analog multiplexer 21. The signal values D are sequentially converted by the A/D converter 20 to the signal values D in a digital value, and are sequentially stored in a storage 23. According to the present embodiment, the readout process is performed while sequentially applying on voltage to the lines L1 to Lx of the scanning line 5 from the gate driver 15b of the scanning driver 15. With this, signal values D can be read from all of the radiation detecting elements 7.

A controller 22 includes a computer in which a CPU (Central Processing Unit), a ROM (Read Only Memory), a RAM (Random Access Memory), an input/output interface, etc. are connected by a bus and a FPGA (Field Programmable Gate Array) (all not shown). The controller 22 may include a dedicated control circuit.

A storage 23 including a SRAM (Static RAM), a SDRAM (Synchronous DRAM), and a NAND type flash memory, and an internal power supply 24 including a lithium ion capacitor, etc. are connected to the controller 22. A communicating unit 30 to perform communication wirelessly or wired with outside devices through the above-described antenna 29 or connector 27 is connected to the controller 22.

As described above, the controller 22 controls the applying of the reverse bias voltage from the bias power supply 14 to the radiation detecting elements 7. The controller 22 controls the operation of units such as the scanning driver 15 and the readout circuit 17 to perform the above-described readout process of the signal value D from the radiation detecting element 7, to store the read out signal value D in the storage 23 or to transfer the stored signal value D to an outside device through the communicating unit 30.

[Configuration of Portable Radiation Image Capturing Apparatus]

Figure 2:
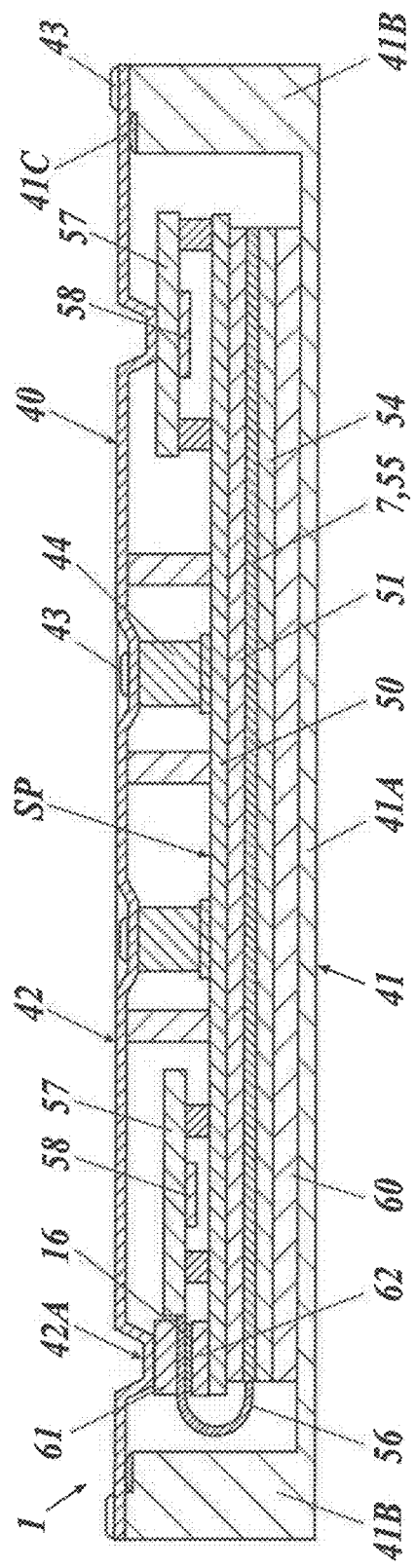
FIG. 2 is a cross-sectional diagram showing a configuration of the portable radiation image capturing apparatus according to the present embodiment.

FIG. 2 is a cross-sectional diagram showing a configuration of a portable radiation image capturing apparatus according to the present embodiment. As shown in FIG. 2, a sensor panel SP (also called a TFT panel) is stored in a case 40 in the radiation image capturing apparatus 1. FIG. 2 shows a state in which the radiation image capturing apparatus 1 is positioned so that a radiation entry surface 41A on which radiation is irradiated is on a lower side of the figure. Hereinbelow, the direction showing top and bottom of the radiation image capturing apparatus 1 is described based on positioning the radiation image capturing apparatus 1 in a state as shown in FIG. 2.

According to the present embodiment, the case 40 of the radiation image capturing apparatus 1 is formed with a front plate 41 including a radiation entry surface 41a formed in a substantial rectangular plate shape and a side wall portion 41B provided standing to surround the outer edges of the radiation entry surface 41A and a back plate 42 formed in a substantial plate shape. According to the present embodiment, for example, the front plate 41 is formed with a fiber reinforced plastic such as a carbon fiber reinforced plastic (CFRP) and a glass fiber reinforced plastic (GFRP). For example, the back plate 42 is formed with a metal such as copper, magnesium, aluminum, iron, etc. The configuration of the back plate 42 is described in detail later.

The back plate 42 is attached to the front plate 41 with a screw 43. According to the present embodiment, the supporting column 44 is provided standing toward the back plate 42 side from a later-described base 50 of the sensor panel SP, and the sensor panel SP is fixed to the back plate 42 by screwing the back plate 42 to the supporting column 44 with the screw 43.

Packing 41C is provided throughout the entire circumference of the side wall portion 41B of the front plate 41. As described above, when the back plate 42 is screwed to the front plate 41 with the screw 43, the back plate 42 is pressed against the packing 41C. With this, the sealability of internal space formed by the front plate 41 and the back plate 42 of the case 40 of the radiation image capturing apparatus 1 is maintained The packing (not shown) is provided not only in the side wall portion 41B of the front plate 41 but also between the screw 43 screwed to the supporting column 44 and the back plate 42, and the sealability of the portion of the screw 43 screwed to the supporting column 44 is maintained The case 40 of the radiation image capturing apparatus 1 does not have to be a configuration provided with a front plate 41 including a side wall portion 41B and a back plate 42 in a substantial plate shape as described above. For example, both the front plate and the back plate may include a side wall portion. When the back plate is attached to the front plate, the front plate may be attached covering the back plate or the back plate may be attached covering the front plate. The configuration is not limited to a specific configuration.

Figure 3:
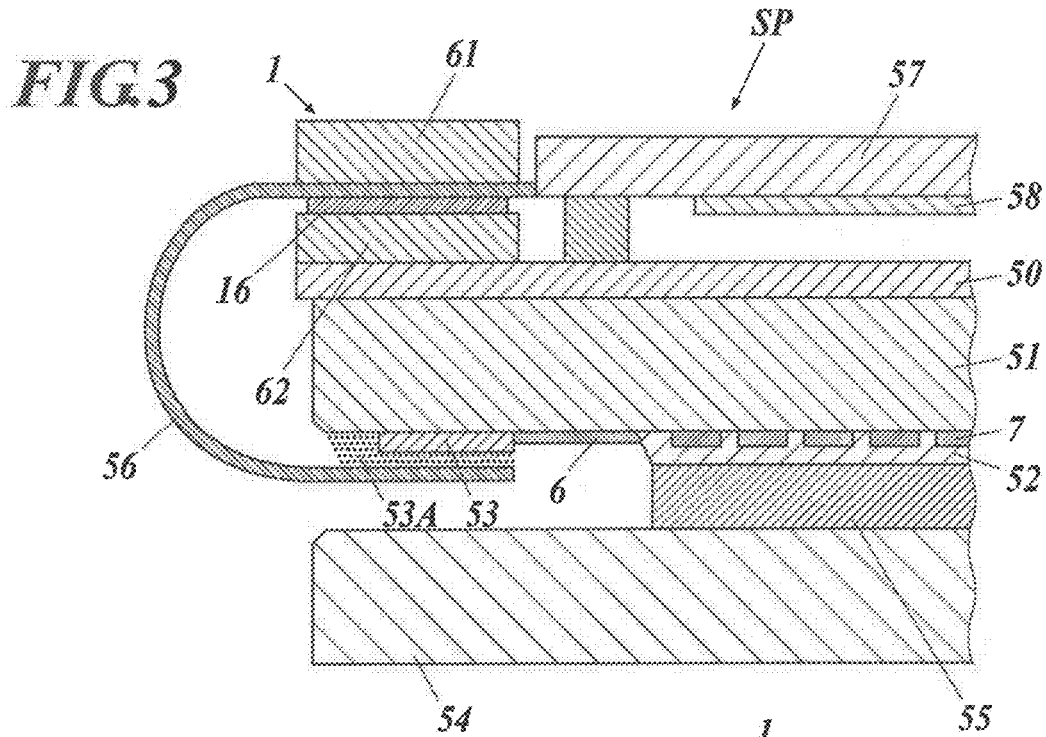
FIG. 3 is an enlarged diagram showing a portion near an edge of a sensor panel of the radiation image capturing apparatus according to the present embodiment.

According to the present embodiment, the sensor panel SP is formed as described below. FIG. 3 is an enlarged diagram of a portion near an edge of the sensor panel SP of the radiation image capturing apparatus 1 according to the present embodiment. In FIG. 3 and the later described FIG. 5, the relative size and thickness of the base 50, readout IC 16, sensor substrate 51, the radiation detecting element 7, scintillator substrate 54, and scintillator 55, do not reflect the relative size and thickness in the actual radiation image capturing apparatus 1. Hereinbelow, the surface of the substrate on the side facing the radiation entry surface 41A of the front plate 41 (that is, surface on bottom side of the figure) is to be the front surface, and the surface on the side facing the back plate 42 (that is, surface on upper side of the figure) is to be the back surface.

The sensor panel SP includes a base 50 including a metallic layer (not shown) such as lead which shields radiation. The sensor substrate 51 including a glass substrate is provided on the front surface side of the base 50.

The above-described plurality of radiation detecting elements 7 are arranged two-dimensionally on the surface of the sensor substrate 51, and a flattening layer 52 is formed with an acrylic resin to cover the radiation detecting elements 7. A plurality of input/output terminals 53 are formed in the surrounding of the surface of the sensor substrate 51, and the above-described signal lines 6 (see FIG. 1) are pulled out to be connected to the input/output terminals 53.

A scintillator 55 is formed on the surface of one side of the scintillator substrate 54 including a glass substrate. According to the present embodiment, a scintillator including phosphor columnar crystals in which phosphor in which light emitting center matter is activated is grown in a columnar shape in a mother material such as Cs1:T1 is employed as the scintillator 55, but the scintillator 55 is not limited to the above. For example, phosphor in a paste form can be applied to the scintillator substrate 54 to form an applied type scintillator.

According to the present embodiment, the sensor substrate 51 and the scintillator substrate 54 are positioned so that the tip of the scintillator 55 comes into contact with the flattening layer 52 covering the radiation detecting elements 7. The sensor substrate 51 and the scintillator substrate 54 are attached to each other with an adhesive (not shown) at a portion on the outer side of the flattening layer 52 and the scintillator 55 (portion describing the signal line 6 in FIG. 3).

A flexible circuit substrate 56 in which a chip such as the readout IC 16, etc. is embedded on a film is connected to the input/output terminal 53 through an anisotropic conductive adhesive material 53A such as an anisotropic conductive film or anisotropic conductive paste. The flexible circuit substrate 56 is connected to the PCB substrate 57 pulled to the back surface side of the base 50. Although illustration is omitted, the wiring of the flexible circuit substrate 56 and the wiring formed on the PCB substrate 57 are connected.

According to FIG. 2 and FIG. 3, the readout IC 16 is provided on an inner surface side of a bent flexible circuit substrate 56 but the readout IC 16 can be provided on an outer surface side of the bent flexible circuit substrate 56. However, in either case, the readout IC 16 is provided in a position near the PCB substrate 56 on the flexible circuit substrate 56, and the readout IC 16 is positioned on the back surface side of the base 50 (that is, a state facing the back plate 42).

The circuits such as the above-described controller 22 or storage 23 (see FIG. 1) or electronic members, etc. (hereinafter collectively referred to as electronic device 58) are provided on the PCB substrate 57. The electronic device 58 includes a power supply circuit 59 (see later-described FIG. 5) which converts and adjusts voltage to be suitable for the functional units such as the readout IC 16, etc. which are supplied with the power supplied from the internal power supply 24 (see FIG. 1). FIG. 2 describes the electronic device 58 positioned in one surface side of the PCB substrate 57 (front surface in the present embodiment, but the electronic device 58 can be positioned on the back surface side of the PCB substrate 57 (or both the front surface side and the back surface side).

For example, when the readout process of the signal value D as described above is performed, the charge generated in the radiation detecting elements 7 flows through the signal line 6 and the flexible circuit substrate 56 and is transmitted to the back surface side of the sensor panel SP, that is, the back plate 42 side. The charge is read out as the signal value D in the readout IC 16, and is stored in the storage 23 on the PCB substrate 57.

According to the present embodiment, the sensor panel SP is formed as described above. The electronic components which generate heat when the signal value D is read out, for example, the readout IC 16 and the power supply circuit 59 are provided on the back plate 42 side of the sensor panel SP. As shown in FIG. 2, a spacer 60 is provided between the scintillator substrate 54 and the front plate 41.

[Configuration Regarding Releasing Heat of Electronic Component]

Next, the configuration regarding releasing heat of the electronic component in the radiation image capturing apparatus 1 according to the present embodiment is described. The effect of the radiation image capturing apparatus 1 according to the present embodiment is also described.

The electronic components as the target of heat release are the electronic components which are used to read out the charge generated in the radiation detecting element 7 when capturing is performed as a signal value D and which generates heat when the signal value D is read out. Such electronic components include, a readout IC 16, and the electronic device 58 such as the power supply circuit 59. The description below describes an example in which the electronic component as the target of heat release is the readout IC 16.

According to the present embodiment, as shown in FIG. 2, etc., a heat conductive member 61 is provided between the readout IC 16 which is the electronic component as the target of heat release and the back plate 42. Specifically, according to the present embodiment, the heat conductive member 61 is provided between the surface of the readout IC 16 facing the back plate 42 and the back plate 42.

The heat conductive member 61 is pressed by the back plate 42 and the readout IC 16 when the back plate 42 is attached to the front plate 41. With this, the above are provided so that the heat conductive member 61 is in close contact with the readout IC 16 and the heat conductive member 61 is in close contact with the back plate 42.

As described above, according to the above-described configuration, when the back plate 42 is attached to the front plate 41 screwed with the screw 43 and the back plate 42 becomes close to the sensor panel SP, the heat conductive member 61 positioned between the readout IC 16 and the back plate 42 is pressed by the back plate 42, and the heat conductive member 61 is in close contact with the readout IC 16. The heat conductive member 61 is also in close contact with the back plate 42.

When the screwing of the back plate 42 to the front plate 41 is complete, the heat conductive member 61 is pressed squeezed between the readout IC 16 and the back plate 42, and the heat conductive member 61 is in close contact with the readout IC 16. Further, the heat conductive member 61 is in close contact with the back plate 42.

Therefore, the readout IC 16, the heat conductive member 61, and the back plate 42 are in close contact with each other and the heat conductive path from the readout IC 16 to the back plate 42 is securely formed. Therefore, the heat generated in the readout IC 16 is securely conducted from the readout IC 16 to the back plate 42. In addition, since the heat conductive path (that is, thickness of the heat conductive member 61) is short, the heat generated in the readout IC 16 can be released outside of the case 40 of the radiation image capturing apparatus 1 from the back plate 42.

Therefore, according to the radiation image capturing apparatus 1 of the present embodiment, the heat generated in the readout IC 16 is not trapped in the case 40 of the radiation image capturing apparatus 1, and can be accurately released outside the apparatus. Therefore, the release of the heat of the readout IC 16 to outside the case 40 can be efficiently performed.

As the heat conductive member 61, for example, ethylene propylene rubber (EPR, EPDM) such as cool provide (registered trademark) and heat conductive sheet, heat conductive double-sided adhesive tape, or heat conductive spacer including a silicon or acrylic heat conductive layer can be used.

If the heat conductive member 61 includes a certain amount of flexibility, the heat conductive member 61 can include shock absorption. Even when shock is provided to the case 40 of the radiation image capturing apparatus 1, the heat conductive member 61 absorbs the shock. Therefore, the shock is not transmitted to the readout IC 16 or the electronic components such as the power supply circuit 59 (or the shock transmitted to the readout IC 16 is reduced).

According to the present embodiment, a projection 42A projecting to the heat conducive member 61 side is formed in the back plate 42 in a position on the inner surface side in contact with the heat conducting member 61. When the back plate 42 is attached to the front plate 41, the heat conducting member 61 is pressed by the projection 42A of the back plate 42 and the readout IC 16.

According to the above configuration, compared to pressing the heat conducting member 61 with the flat back plate 42, the force is transmitted more accurately to the heat conductive member 61 by pressing with the projection 42A of the back plate 42. Therefore, compared to being pressed by a flat back plate 42, the heat conductive member 61 is pressed and squeezed more between the readout IC 16 and the back plate 42 when pressed with the projection 42A of the back plate 42. Therefore, the heat conductive member 61 is in closer contact with the readout IC 16. Further, the heat conductive member 61 is in closer contact with the back plate 42.

Therefore, the heat conducting path (that is, the thickness of the heat conductive member 61) becomes even shorter, and the heat conductive member 61, the readout IC 16, and the back plate 42 come into contact even closer. With this, the heat release efficiency to release the heat generated in the readout IC 16 to outside the case 40 is enhanced The projection 42A to the inner surface side of the back plate 42 can be formed by denting the back plate 42 toward the inside as shown in FIG. 2. According to the above configuration, the projection 42A can be easily formed. Other than the above, for example, the projection 42A can be formed by forming this position of the back plate 42 thickly.

Figure 4A:
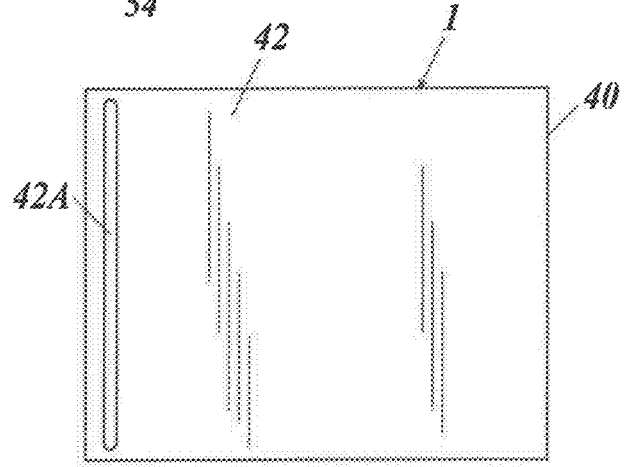
FIG. 4A is a diagram showing a projection of a back plate formed in a straight line shape.

For example, a plurality of readout IC 16 may be arranged aligned on the left side of FIG. 2 in a direction orthogonal to the sheet. In this case, for example, as shown in FIG. 4A viewing the back plate 42 from outside, the projection 42A (a projection 42A shaped like one ridge when viewing the back plate 42 from the inside) is formed denting to the inside in a straight line shape the position of the back plate 42 corresponding to the portion where the plurality of readout IC 16 (not shown in FIG. 4A and FIG. 4B) are aligned. Then, all of the heat conductive members 61 (not shown in FIG. 4A and FIG. 4B) attached to the readout IC 16 can be pressed by one projection 42A.

Figure 4B:
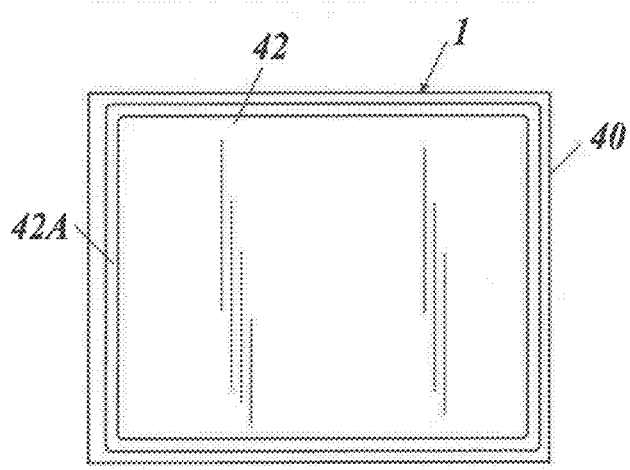
FIG. 4B is a diagram showing a projection of a back plate formed in an annular shape.

As shown in FIG. 4B, the projection 42A can be formed in annular (annular square) surrounding the entire edge of the back plate 42 (that is, a projection 42A of the back plate 42 shaped in an annular ridge when viewing the back plate 42 from inside). An annular projection 42A is not limited to one, and a plurality of projections 42A can be provided.

According to the above configuration, similar to providing bumps in an iron plate to enhance the strength of the iron plate, it is possible to enhance the strength (specifically, strength against bending and twisting) of the back plate 42 in a substantial plate shape, and the strength of the radiation image capturing apparatus 1 itself can be enhanced. The thickness of the heat conductive member 61 can be reduced in the amount of the distance that the back plate 42 is projected toward the inner surface side. The density of the heat conductive member 61 is about the same as light metal such as aluminum and magnesium. This influences the weight of the apparatus, and the entire apparatus can be made lighter by making the heat conductive member 61 thinner. By making the heat conducive member 61 thinner, the heat resistance from the readout IC 16 as the heat generating source to the back plate 42 can be made small, and the heat release efficiency is enhanced. When the readout IC 16 is not generating heat such as when the radiation image capturing apparatus 1 is being moved, the radiation technician can hook his finger to the projection 42A which projects to the inside of the back plate 42. With this, it becomes easy to transport the radiation image capturing apparatus 1.

When the thickness of the heat conductive member 61 is formed to be 0. 5 mm to 6 mm, it is possible to configure a radiation image capturing apparatus with a thickness suitable for the standards of cassette sizes such as JISZ4095 while maintaining heat releasing properties. However, when the thickness is thin, the external shock is easily transmitted to the readout IC 16. This leads to the image being blurred or the IC breaking. When the thickness is thick, the weight of the apparatus increases as described above, and the advantage of the apparatus being portable is lost. Therefore, preferably, the thickness is 1 mm to 3 mm.

As described above, when the back plate 42 is formed with a metal, typically, since metal has a higher heat conductivity than plastic, the heat from the readout IC 16 can be diffused and released immediately by the back plate 42, and the efficiency to release the heat generated in the readout IC 16 to outside the case 40 can be enhanced.

By forming fine dents and bumps on the outer surface side of the back plate 42 to increase surface area, and by painting heat releasing paint with high heat conductivity and emissivity on the outer surface side, the heat releasing efficiency of the heat generated by the read out IC 16 to the outside of the case 40 can be enhanced even more. The emissivity can be enhanced by surface processes such as applying a resin film with an emissivity higher than metal to enhance the heat releasing efficiency. By performing the surface process on the outer surface side of the back plate 42, there is also the advantage that slipping can be prevented when the radiation image capturing apparatus 1 is carried. With this, it becomes easy to transport the radiation image capturing apparatus 1.

According to the radiation image capturing apparatus 1, the electronic components used to read out the charge generated in the radiation detecting element 7 as the signal value D and which generates heat when the signal value D is read out is not limited to the above-described readout IC 16, and the power supply circuit 59 which supplies power to the functional units such as the readout IC 16 is also included. The same configuration as the configuration to release heat of the readout IC 16 is used to release the heat generated in the power supply circuit 59 to outside the back plate 42.

Figure 5:
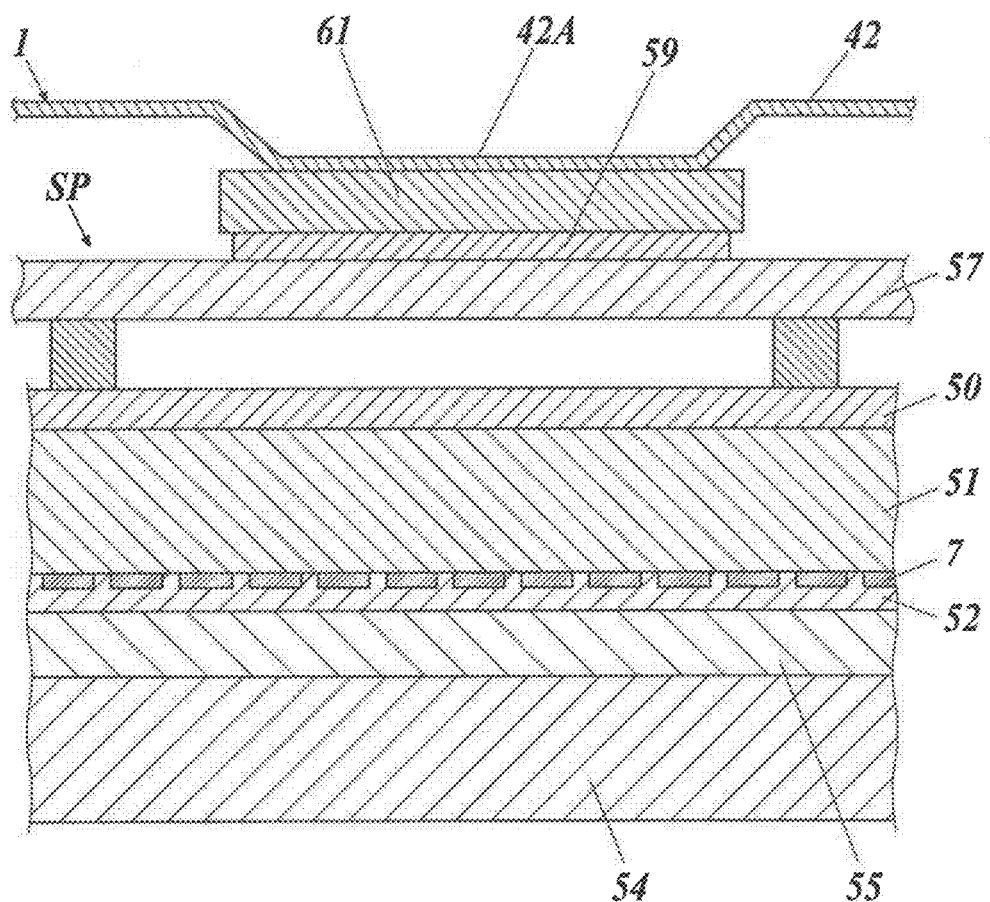
FIG. 5 is an enlarged diagram showing a heat conduction member provided between a power supply circuit and a back plate.

As shown in FIG. 5, specifically, the heat conductive member 61 is provided in the back plate 42 of the base 50 of the sensor panel SP, between the power supply circuit 59 provided on the PCB substrate 57 of (or the face facing the back plate 42 of the power supply circuit 59) and the back plate 42 (or the projection 42A of the back plate 42). The heat conductive member 61 is pressed between the back plate 42 and the power supply circuit 59 when the back plate 42 is attached to the front plate 41. With this, the heat conductive member 61 is in close contact with the power supply circuit 59. Further, the heat conductive member 61 is in close contact with the back plate 42 (or projection 42A, same applies hereinafter).

When the back plate 42 is attached to the front plate 41, the heat conductive member 61 is pressed and squeezed between the power supply circuit 59 and the back plate 42. With this, the heat conductive member 61 is securely in close contact with the power supply circuit 59 and the back plate 42. Therefore, the heat is securely conducted from the power supply circuit 59 to the back plate 42 through the heat conductive member 61. With this, since the heat conductive path (that is, the thickness of the heat conductive material 61) becomes short, the heat generated in the power supply circuit 59 can be released outside of the case 40 of the radiation image capturing apparatus 1 from the back plate 42.

Therefore, according to the above configuration, the heat generated by the electronic components such as the power supply circuit 59 is not trapped in the case 40 of the radiation image capturing apparatus 1, and the heat can be accurately released outside of the apparatus. With this, the release of the heat of the readout IC 16 to outside the case 40 can be performed very efficiently. The illustration of the front plate 41 is omitted in FIG. 5.

As shown in FIG. 2, when the back plate 42 is attached to the front plate 41, a supporting member 62 can be provided between the readout IC 16 and the base 50 of the sensor panel SP so that the readout IC 16 is not pushed and moved toward the sensor panel SP side by the back plate 42 (or the projection 42A, same applies below) which comes near the sensor panel SP side.

In FIG. 5, the supporting member 62 is not provided between the power supply circuit 59 and the PCB substrate 57. However, the supporting member 62 can be provided between the power supply circuit 59 and the PCB substrate 57 or the base 50 (or between the portion where the power supply circuit 59 is attached to the PCB substrate 57 and the base 50).

Then, the supporting member 62 can be a heat insulating member including heat insulating properties. When the supporting member 62 is formed with the heat insulating member, it is possible to cut the conducting of heat between the electronic component such as the readout IC 16 and the sensor panel SP with the supporting member 62. With this, it is possible to prevent transmitting of the heat generated by the electronic component such as the readout IC 16 to the base 50 of the sensor panel SP.

The heat conducted to the base can be diffused in the surface direction by including metal or fiber reinforced plastic such as carbon fiber reinforced plastic so that the heat conductivity of the base 50 in the surface direction becomes high.

Therefore, for example, the portion of the sensor panel SP near the readout IC 16 is heated, and it is possible to prevent the problems such as the image blurring occurring in the portion of the radiation image corresponding to this portion.

On the other hand, it is possible to configure the supporting member 62 as the heat conductive member including heat conductivity. If the base 50 of the sensor panel SP as described above is formed so that the heat conductivity in the surface direction (left and right direction in FIG. 3) is high, the heat generated in the readout IC 16 and conducted to the base 50 of the sensor panel SP through the supporting member 62 is diffused in the surface direction of the base 50 of the sensor panel SP. Therefore, it is possible to accurately prevent the problem of image blur occurring in the radiation image due to only the portion of the base 50 near the readout IC 16 being locally heated.

Figure 6:
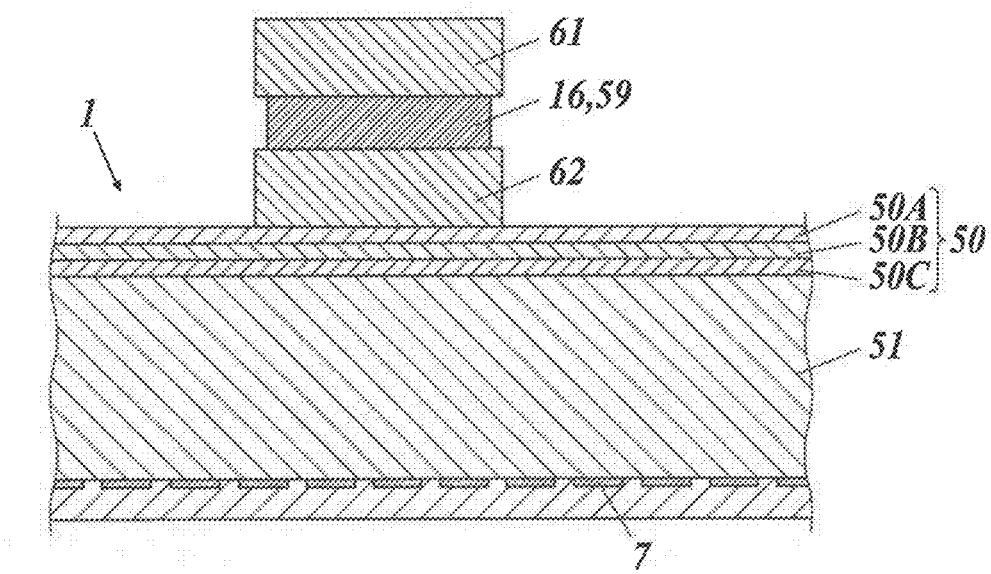
FIG. 6 is an enlarged diagram showing a configuration example of a base of a sensor panel.

In this case, in order to further enhance the conductivity of heat of the base 50 in the sensor panel SP in the surface direction, for example, as shown in FIG. 6, the base 50 can be formed so that the layer 50B with low heat conductivity is placed between the layers 50A, 50C with high heat conductivity (that is, each layer layered).

In order to enhance the heat conductivity and to maintain the rigidity of the base 50, the layers 50A, 50C of the base 50 can include fiber reinforced plastic such as carbon fiber reinforced plastic (CFRP). The layer 50B of the base 50 with low heat conductivity can include Rohacell (registered trademark: hard plastic closed cell foam including polymethacrylimides (PMI) as the base) which is a foam with high hardness.

According to the above configuration, the heat generated in the readout IC 16 and conducted to the base 50 of the sensor panel SP through the supporting member 62 including heat conductivity is not conducted in the direction from the base 50 toward the radiation detecting element 7 (up and down direction in FIG. 6) due to the layer 50B with low heat conductivity in the base 50 of the of the sensor panel SP preventing the conducting. The heat is diffused in the surface direction of the base 50 along the layer 50A of the base 50 extending in the direction orthogonal to the above (left and right direction in FIG. 6).

Therefore, when the base 50 of the sensor panel SP is configured as shown in FIG. 6, it is possible to accurately enhance the heat conductivity in the surface direction of the base 50 orthogonal to the direction from the base 50 to the radiation detecting element 7 than the direction from the base 50 to the radiation detecting element 7. Therefore, the heat is diffused in the surface direction of the base 50. With this, it is possible to accurately prevent the problem of the image blur occurring in the radiation image due to only the portion of the base 50 near the readout IC 16 being heated locally.

In FIG. 6, the illustration of the scintillator 55 and the case 40 is omitted. When not only the heat conductive member 61 but also the supporting member 62 also has flexibility, the supporting member 62 can have shock absorption. According to the above configuration, even when shock is applied to the case 40 of the radiation image capturing apparatus 1, the shock is absorbed by the heat conductive member 61 and the supporting member 62. Therefore, the shock is not transmitted to the readout IC 16 and the electronic components such as the power supply circuit 59 (or the shock transmitted to the readout IC 16 is reduced).

[Effect]

According to the portable radiation image capturing apparatus 1 of the present embodiment, the readout IC 16 and the electronic components such as the power supply circuit 59, etc. which generate heat when the signal value D is read out from the radiation detecting element 7 are provided on the back plate 42 side of the case 40 of the sensor panel SP, and the heat conductive member 61 is provided between the electronic components 16, 59 and back plate 42. When the back plate 42 is attached to the front plate 41, the back plate 42 and the electronic components 16, 59 press the heat conductive member 61. With this, the heat conductive member 61 is provided so that the heat conductive member 61 is in close contact with the electronic components 16, 59, and the heat conductive member 61 is in close contact with the back plate 42.

Therefore, the electronic components 16, 59, the heat conductive member 61, and the back plate 42 are in close contact with each other and the heat conductive path from the electronic components 16, 59 to the back plate 42 is securely formed. With this, the heat generated in the electronic components 16, 59 is securely conducted from the electronic components 16, 59 to the back plate 42. Further, since the heat conducive path (that is, the thickness of the heat conductive member 61) becomes short, the heat generated in the electronic components 16, 59 can be released to the outside of the case 40 of the radiation image capturing apparatus 1 from the back plate 42.

Therefore, the heat generated in the electronic components 16, 59 is not trapped in the case 40 of the radiation image capturing apparatus 1, and can be accurately released to outside the apparatus. With this, the release of the heat of the electronic components 16, 59 to outside the case 40 can be performed with high efficiency.

When the moving image capturing is performed, since the readout process of the signal value D is repeated, the amount of heat generated in the readout IC 16 and the electronic components such as the power supply circuit 59 becomes larger than the simple capturing. However, according to the portable radiation image capturing apparatus 1 of the present embodiment, even when moving image capturing is performed, the heat generated in the readout IC 16 and the electronic components such as the power supply circuit 59 can be released efficiently to outside the case 40 of the radiation image capturing apparatus 1. Therefore, it is possible to accurately prevent problems such as the temperature rising in the sensor panel SP and the case 40 of the radiation image capturing apparatus 1 and the signal value D becoming an abnormal value. With this, the frame images in the moving image capturing can be accurately captured.

The present invention is not limited to the above embodiments, and the present invention can be suitably modified without leaving the scope of the present invention.

Although embodiments if the present invention have been described and illustrated in detail, the disclosed embodiments are made for purposes of illustration and example only and not limitation. The scope of the present invention should be interpreted by terms of the appended claims.

INDUSTRIAL APPLICABILITY

The present invention can be used in the field of radiation image capturing (specifically, medical field).

DESCRIPTION OF REFERENCE NUMERALS

1 radiation image capturing apparatus (portable radiation image capturing apparatus)

7 radiation detecting element
16 readout IC (electronic component)
40 case
41 front plate
42 back plate
42A projection
50 base
59 power supply circuit (electronic component)
61 heat conductive member
62 supporting member (heat conductive member, heat insulating member)
D signal value
SP sensor panel

The invention claimed is:

1. A portable radiation image capturing apparatus provide with a sensor panel in which a plurality of radiation detecting elements are arranged two-dimensionally and a case which is formed with a front plate on a side where radiation enters and a back plate on an opposite side, wherein the sensor panel is stored in the case, the portable radiation image capturing apparatus comprising:
   an electronic component which is provided on the back plate side of the sensor panel and which generates heat when charge generated in the radiation detecting element is read out as a signal value; and
   a heat conductive member which is provided between the electronic component and the back plate,
   wherein the back plate presses the heat conductive member toward the electronic component when the back plate is connected to the front plate to form the case so that the heat conductive member is pressed between the back plate and the electronic component in a state in which the heat conductive member is in close contact with the electronic component and the heat conductive member is in close contact with the back plate.

2. The portable radiation image capturing apparatus according to claim 1, wherein the electronic component includes a readout IC which reads out the charge generated in the radiation detecting element as the signal value.

3. The portable radiation image capturing apparatus according to claim 1, wherein,
   a projection which projects to the heat conductive member side is formed on the back plate in a position on an inner surface side which comes into contact with the heat conductive member, and
   the heat conductive member is pressed by the projection of the back plate and the electronic component.

4. The portable radiation image capturing apparatus according to claim 3, wherein the heat conductive member has a thickness within a range of 1 mm to 3 mm.

5. The portable radiation image capturing apparatus according to claim 4, wherein the projection of the back plate is formed in an annular ridge shape.

6. The portable radiation image capturing apparatus according to claim 4, wherein the projection of the back plate is formed by denting the back plate toward the inside.

7. The portable radiation image capturing apparatus according to claim 1, wherein the back plate is formed with metal.

8. The portable radiation image capturing apparatus according to claim 7, wherein a surface process which enhances at least one among surface area, heat conductivity, and emissivity is performed on an outer surface side of the back plate.

9. The portable radiation image capturing apparatus according to claim 1, wherein,
   the sensor panel includes a sensor substrate provided with the radiation detecting element and a base which is positioned on an opposite side of a side where the radiation enters the sensor substrate and which supports the sensor substrate,
   the electronic component is provided on the back plate side of the base, and
   the heat conductive member is provided between the electronic component and the base.

10. The portable radiation image capturing apparatus according to claim 9, wherein,
    the electronic component is provided on the back plate side of the base of the sensor panel, and
    heat conductivity of the base is higher in a surface direction orthogonal to a direction from the base towards the radiation detecting element than the direction from the base towards the radiation detecting element.

11. The portable radiation image capturing apparatus according to claim 1, wherein,
    the sensor panel includes a sensor substrate provided with the radiation detecting element and a base which is positioned on an opposite side of a side where the radiation enters the sensor substrate and which supports the sensor substrate,
    the electronic component is mounted on the back plate side of the base, and
    a heat insulating member is provided between the electronic component and the base.

12. The portable radiation image capturing apparatus according to claim 1, wherein the electronic component is mounted on the back plate side of the sensor panel.

13. The portable radiation image capturing apparatus according to claim 1, wherein the heat conductive member is squeezed between the back plate and the electronic component.

* * * * *